(12) United States Patent
Robinson

(10) Patent No.: US 9,107,708 B2
(45) Date of Patent: Aug. 18, 2015

(54) LAMINOPLASTY SYSTEM

(71) Applicant: James C. Robinson, Atlanta, GA (US)

(72) Inventor: James C. Robinson, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 198 days.

(21) Appl. No.: 13/655,432

(22) Filed: Nov. 19, 2012

(65) Prior Publication Data

US 2014/0142637 A1 May 22, 2014

(51) Int. Cl.
*A61B 17/58* (2006.01)
*A61B 17/60* (2006.01)
*A61F 2/00* (2006.01)
*A61B 17/70* (2006.01)
*A61B 17/80* (2006.01)

(52) U.S. Cl.
CPC .......... *A61B 17/7071* (2013.01); *A61B 17/808* (2013.01)

(58) Field of Classification Search
CPC .................. A61B 17/3421; A61B 17/3468
USPC .......................................... 606/104, 323, 105
See application file for complete search history.

(56) References Cited

U.S. PATENT DOCUMENTS 5,928,139 A * 7/1999 Koros et al. ............... 600/205
8,152,720 B2 * 4/2012 Loftus et al. ............... 600/215

\* cited by examiner

*Primary Examiner* — Andrew Yang
(74) *Attorney, Agent, or Firm* — FisherBroyles, LLP; Anthony J. DoVale

(57) ABSTRACT

A laminoplasty plate for securing a separated lamina portion of a desired cervical vertebra in a relief position and a method of using the same to perform a laminoplasty. In one aspect, a lamina setting tool is presented for positioning the lamina portion of the desired cervical vertebra in the relief position. In one aspect, the tool has a first sidewall section that slides in longitudinal relation to a second sidewall section.

25 Claims, 13 Drawing Sheets

LAMINOPLASTY SYSTEM

FIELD OF THE INVENTION

The present invention relates generally to surgical procedures, most particularly for use in performing a laminoplasty to treat cervical stenosis in the spine. More specifically, the invention pertains to a method for increasing the area of the spinal canal by securing a separated lamina portion of a desired cervical vertebra in a relief position.

BACKGROUND OF THE INVENTION

Spinal stenosis is a pathology of the spine that involves the narrowing of the spinal canal, through which the spinal cord and nerve roots run. This narrowing may be congenital and, consequently, can affect patients at any age. Spinal stenosis may result from thickening and calcification of spinal ligaments. For example, calcification can result from deposits of calcium salts within the spine. In addition, spinal stenosis can result when bones and joints are enlarged, leading to the formation of osteophytes (bone spurs). A significant cause of osteophytes is spondylosis, in which spinal discs lose water and become less dense. Also, a bulging or herniated disc may place pressure on the spinal cord or nerve root such that the area of the spinal canal is reduced. Finally, diseased bone or tumors can extend into the spinal cord area, decreasing the space available for nerve roots within the spinal canal.

Compression of the spinal cord resulting from spinal stenosis can produce pain, weakness, or loss of feeling in the patient. Additionally, spinal cord compression can lead to myelopathy, which causes neurological damage and results in spinal cord malfunction. If left untreated, the compression can eventually damage the circulatory system within the spinal cord, leading to more severe myelopathy.

Two surgical methods are traditionally used to decompress the spinal cord from a posterior approach to the spine. First, the laminectomy involves the removal of the lamina and spinous processes in order to expose the dura covering the spinal cord. Due to the removal of portions of the supporting structures at the posterior of the vertebra that are used to align the spinal column, a laminectomy can create postural deformities in patients. In addition, there is a risk that the procedure will lead to substantial scar formation in the patient. In order to address these concerns, a graft may be installed between the vertebral bones involved to promote fusion. However, this may lead to a decrease in the range of motion in the spine, and there may also be accelerated degeneration of the vertebrae above and below the repaired vertebra.

The second method traditionally used to decompress the spinal cord is the laminoplasty. In a laminoplasty procedure, the targeted vertebra is cut and the lamina repositioned so that the lamina is lifted off the dura and the spinal canal is thus enlarged. Then, a plate and/or a graft are inserted to permanently enlarge the spinal canal. There are generally two techniques used to perform a laminoplasty. First, the unilateral or "open door" laminoplasty involves cutting entirely through a first portion of the lamina on the first side of midline of the targeted vertebra, while a second portion of the lamina on the second side of midline is only cut partially through to create a hinge. Then, the first lamina portion is hinged away from the spinal cord to increase the size of the spinal canal. Finally, a graft and/or plate is inserted into the opening to permanently enlarge the spinal canal. Second, the bilateral or "French door" laminoplasty involves cutting entirely through the midline of the spinous process, and then cutting partially through both sides of the lamina portion, creating two hinges. The vertebra can then be opened at the bisected spinous process, and a graft or plate can be inserted into the opening to permanently enlarge the spinal canal.

Unlike the laminectomy, the laminoplasty does not involve the excising of any bone material. In addition, when compared to the laminectomy, the laminoplasty may provide greater stability. A wider range of motion for the patient is maintained compared to a fusion. Through the use of laminar fusion and fixation techniques in a laminoplasty procedure, the achieved decompression and position of the displaced lamina can be more effectively maintained.

Despite the advances that have been achieved in laminoplasty procedures, there are still some limitations in the effectiveness of the procedures and the ease with which the procedures are completed, especially when performed on the cervical vertebrae. For example, the present technique requires the surgeon to make a large incision to reach the spine, which includes stripping of muscle and ligament attachments to the bone, and this can lead to significant muscle and tissue damage. In addition, in cervical spine surgeries, the smaller size of the target vertebra makes the operation more complicated. For instance, the surgeon may find it difficult to make precise adjustments within the operating space or to know whether the lamina has been displaced an appropriate distance. Further, in some patients, the increase in area that can be achieved by current techniques is insufficient to provide complete relief from spinal cord compression. Finally, due to the uneven nature of "open door" laminaplasties, patients may have a slight imbalance in their spines following the procedure, and the increase in spinal canal diameter is asymmetric.

Similarly, the laminoplasty plates that are currently used also have limitations. For example, many current laminoplasty plates are too large in size for insertion into small incisions or for effective attachment to cervical vertebrae. In addition, current plates frequently lack the stability required to permanently orient the lamina in an appropriate position. Also, the design of existing laminoplasty plates often makes the process of attaching the plate to the vertebra and lamina very challenging. Finally, many existing laminoplasty plates are not adequately constructed to allow for conjunctive use of bone fusion material. Existing plates are also cumbersome for use with less invasive surgical procedures.

Accordingly, it remains desirable in the pertinent art to provide laminoplasty plates to address the limitations associated with known plates, including but not limited to those limitations discussed above. Additionally, it is desirable in the pertinent art to provide methods and systems for using the said laminoplasty plates to address the limitations associated with known methods and systems, including but not limited to those limitations discussed above.

SUMMARY

Presented herein is a laminoplasty plate for securing a separated lamina portion of a desired cervical vertebra in a relief position and a method of using the same to perform a laminoplasty. In one aspect, the laminoplasty plate comprises a proximal end portion having a bottom surface defined in a first plane and a distal end portion having a bottom surface defined in a second plane.

In one aspect, a lamina setting tool is presented for positioning the lamina portion of the desired cervical vertebra in the relief position. In one aspect, the tool comprises In another aspect, the lamina portion is controllably elevated to a relief position in which the spinal canal of the desired cervical vertebra has a relief cross-sectional area that is greater than the pre-operative cross-sectional area, wherein the lamina portion is subsequently secured in an elevated position.

In a further aspect, the lamina setting tool can be provided to assist with the step of controllably raising and securing the lamina portion in the relief position. In this aspect, the guide is configured to detachably mount to the mountable portion of the laminoplasty plate.

Related methods of operation are also provided. Other apparatuses, methods, systems, features, and advantages of the laminoplasty plates and the method of their use will be or become apparent to one with skill in the art upon examination of the following figures and detailed description. It is intended that all such additional apparatuses, methods, systems, features, and advantages be included within this description, be within the scope of the laminoplasty plates and the method of their use, and be protected by the accompanying claims.

DESCRIPTION OF THE INVENTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Figure 1:
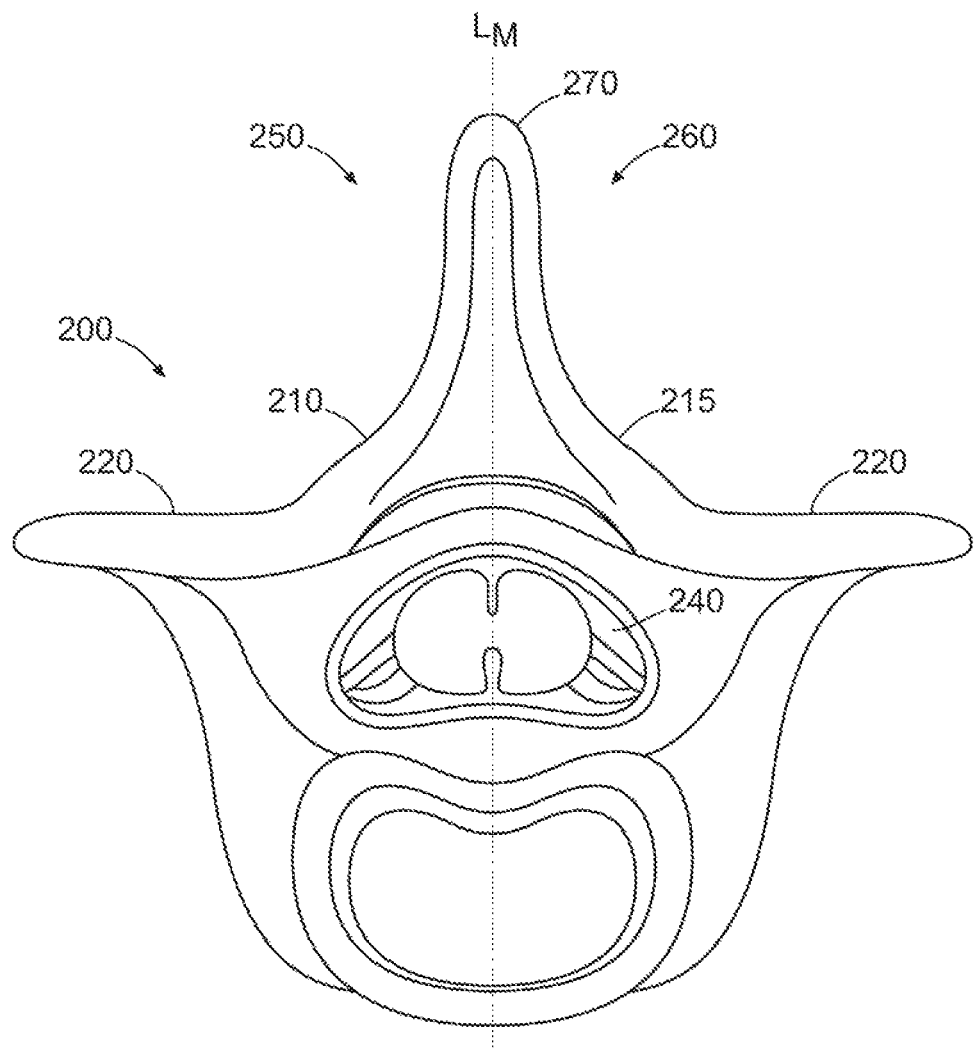
FIG. 1 is top plan view of an exemplified cervical vertebra showing the spinal canal having a pre-operative cross-sectional area.
Figure 2:
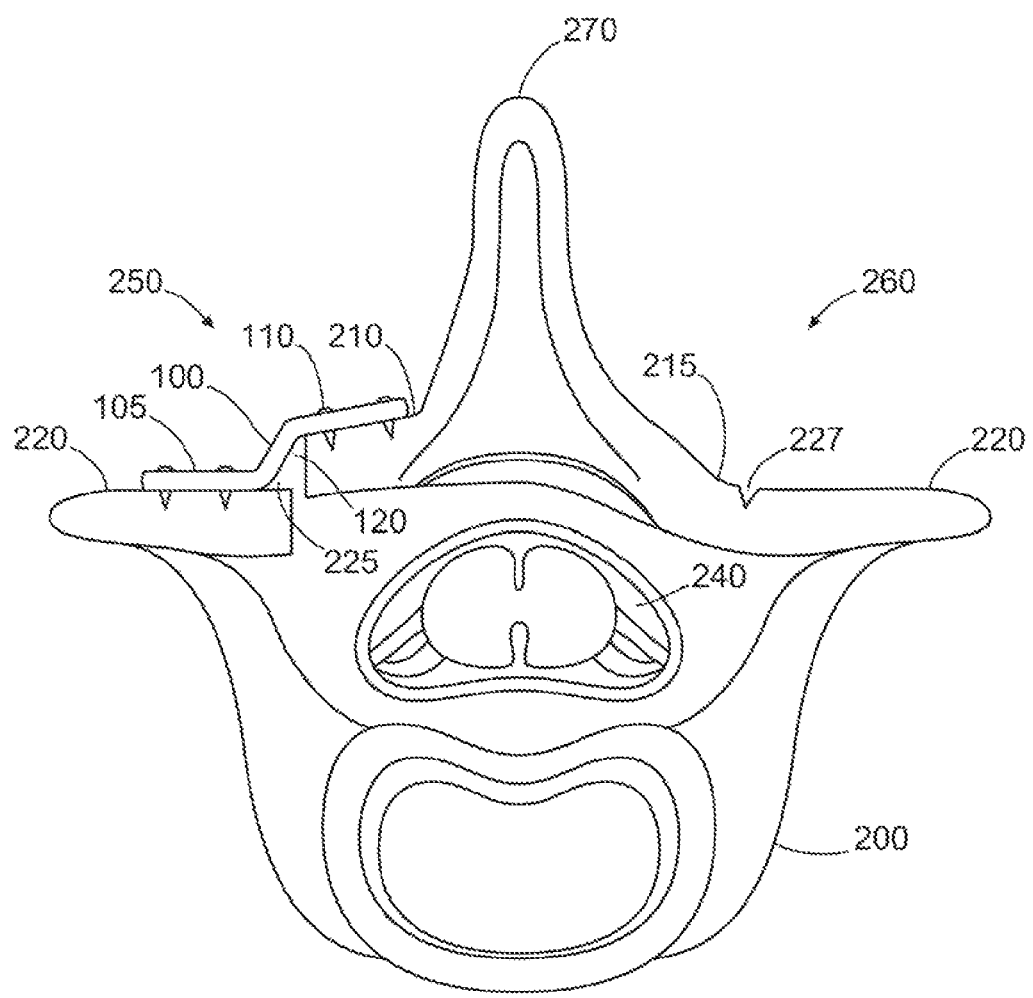
FIG. 2 is a top plan view of the cervical vertebra of FIG. 1, showing a first lamina portion in the relief position.
Figure 3:
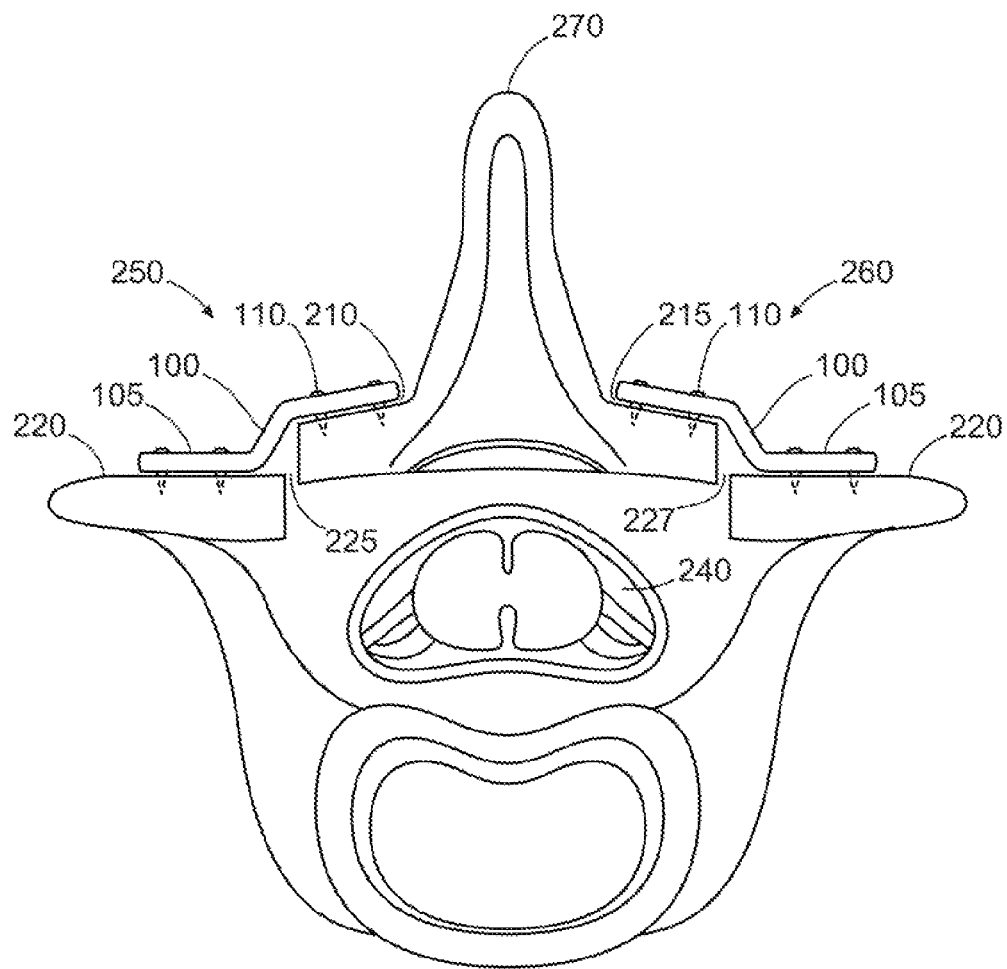
FIG. 3 is a top plan view of the cervical vertebra of FIG. 1, showing the first and second lamina portions in the relief position.
Figure 4:
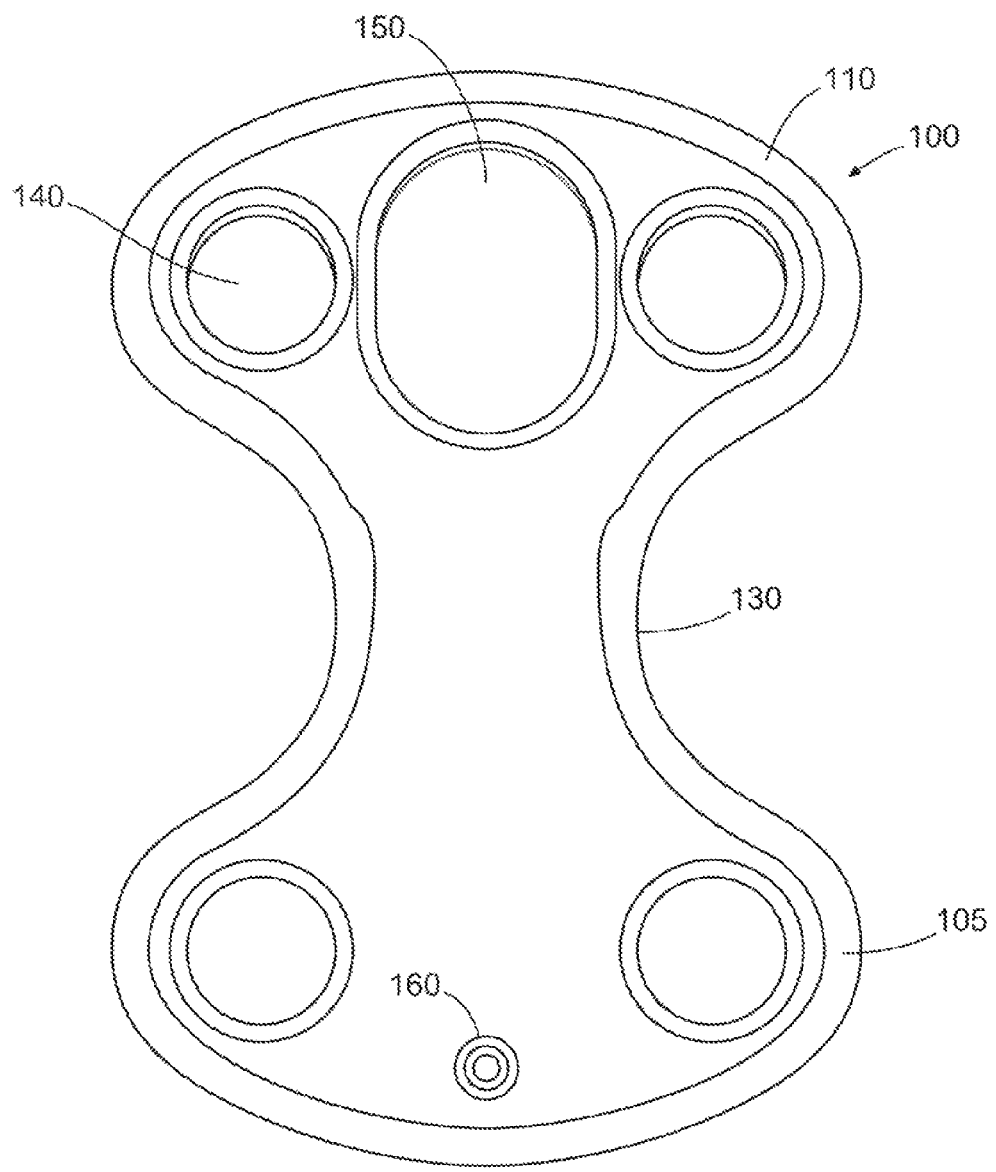
FIG. 4 is a top plan view of an exemplified laminoplasty plate.
Figure 5A:
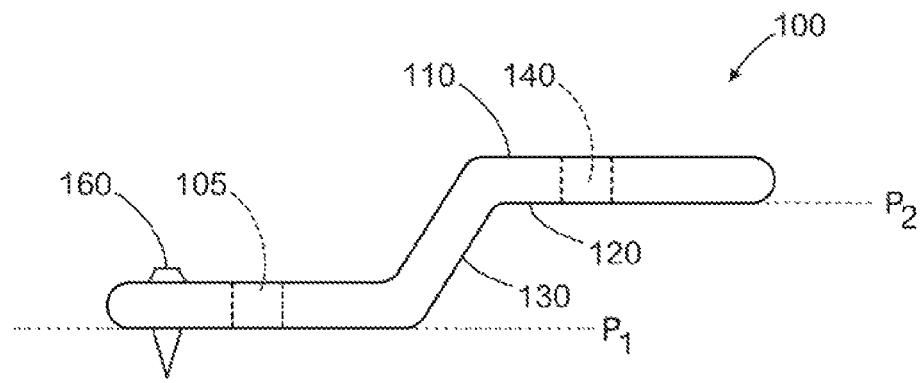
FIG. 5A is a side elevational view of the laminoplasty plate of FIG. 4, showing the first and second planes in parallel.
Figure 5B:
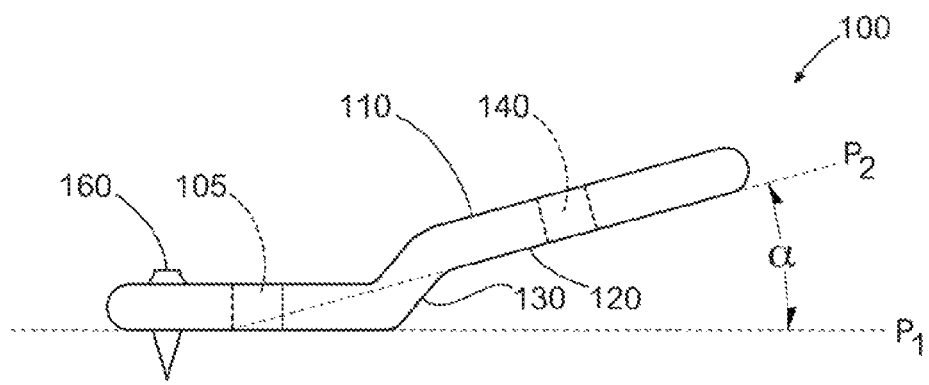
FIG. 5B is a side elevational view of the laminoplasty plate of FIG. 4, showing the first and second planes are at an acute angle relative to one another.
Figure 6:
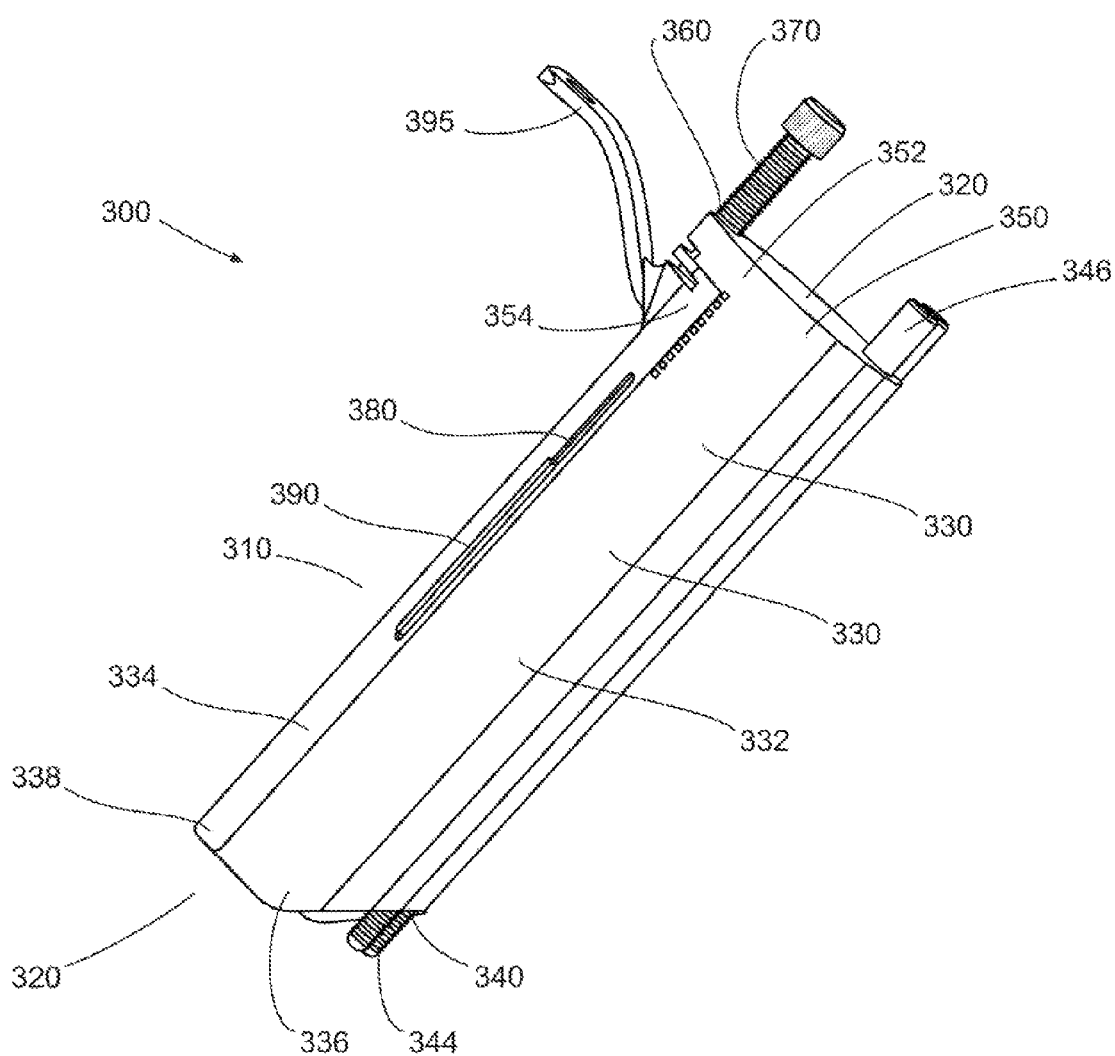
FIG. 6 is a side perspective view of a lamina setting tool.
Figure 7:
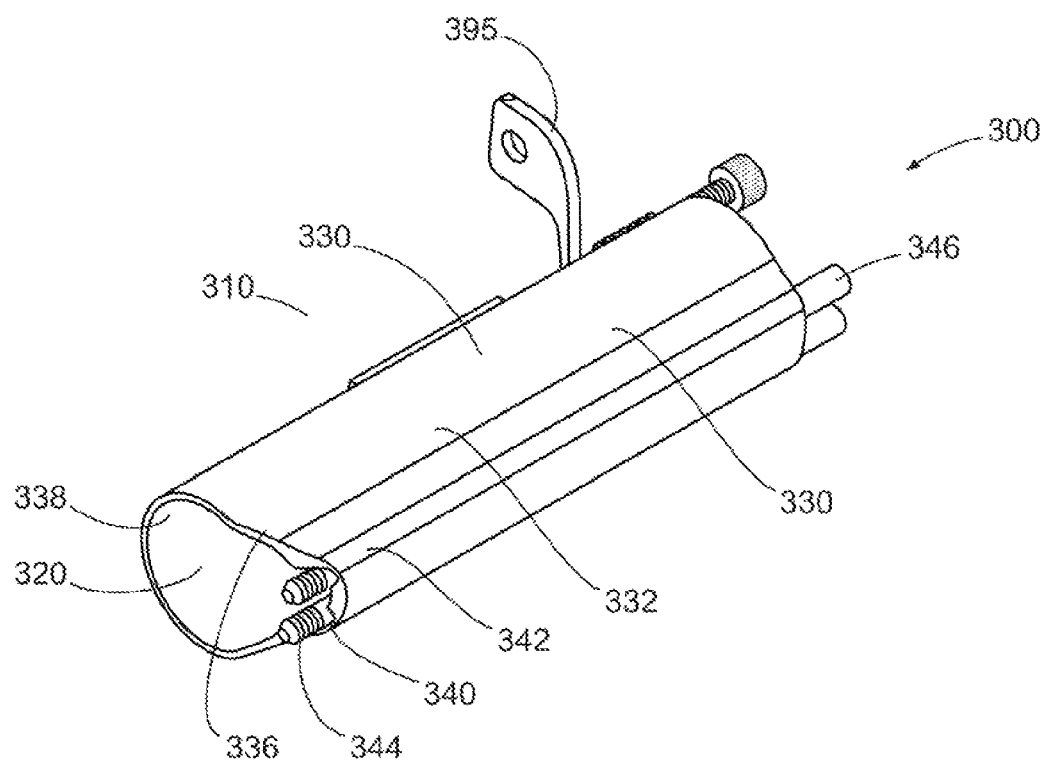
FIG. 7 is a bottom perspective view of the lamina setting tool of FIG. 6.
Figure 8:
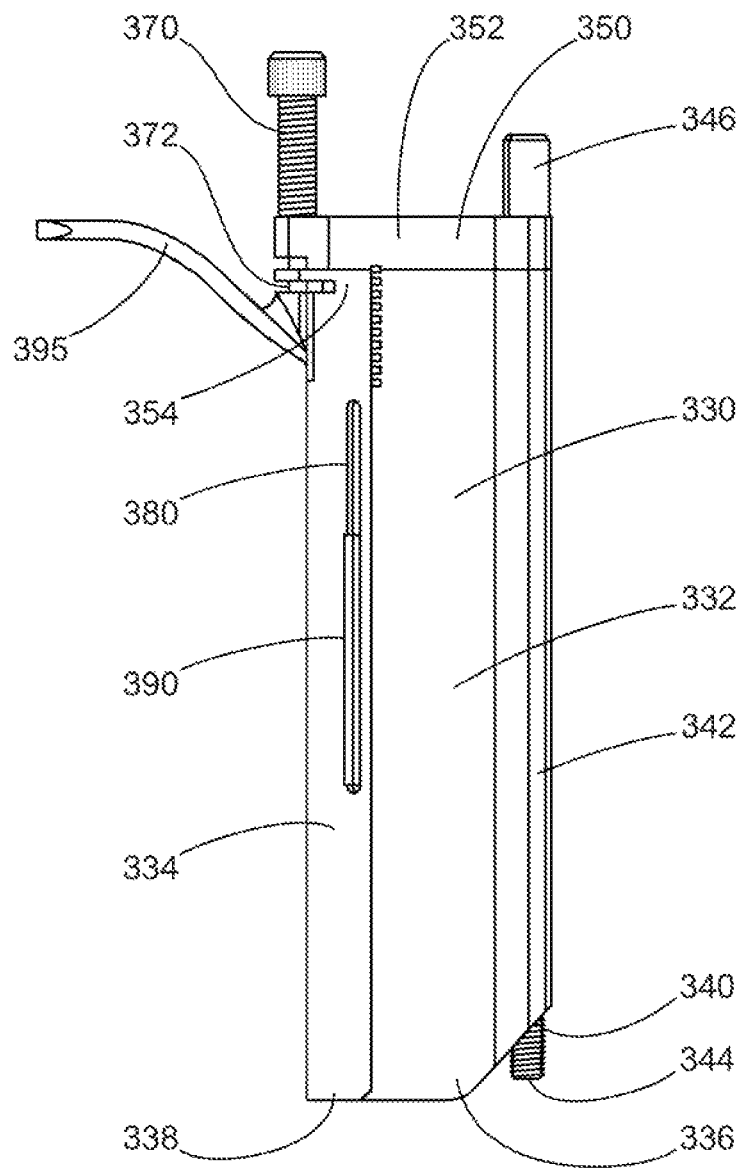
FIG. 8 is a side elevational view of the lamina setting tool of FIG. 6 in the first position.
Figure 9:
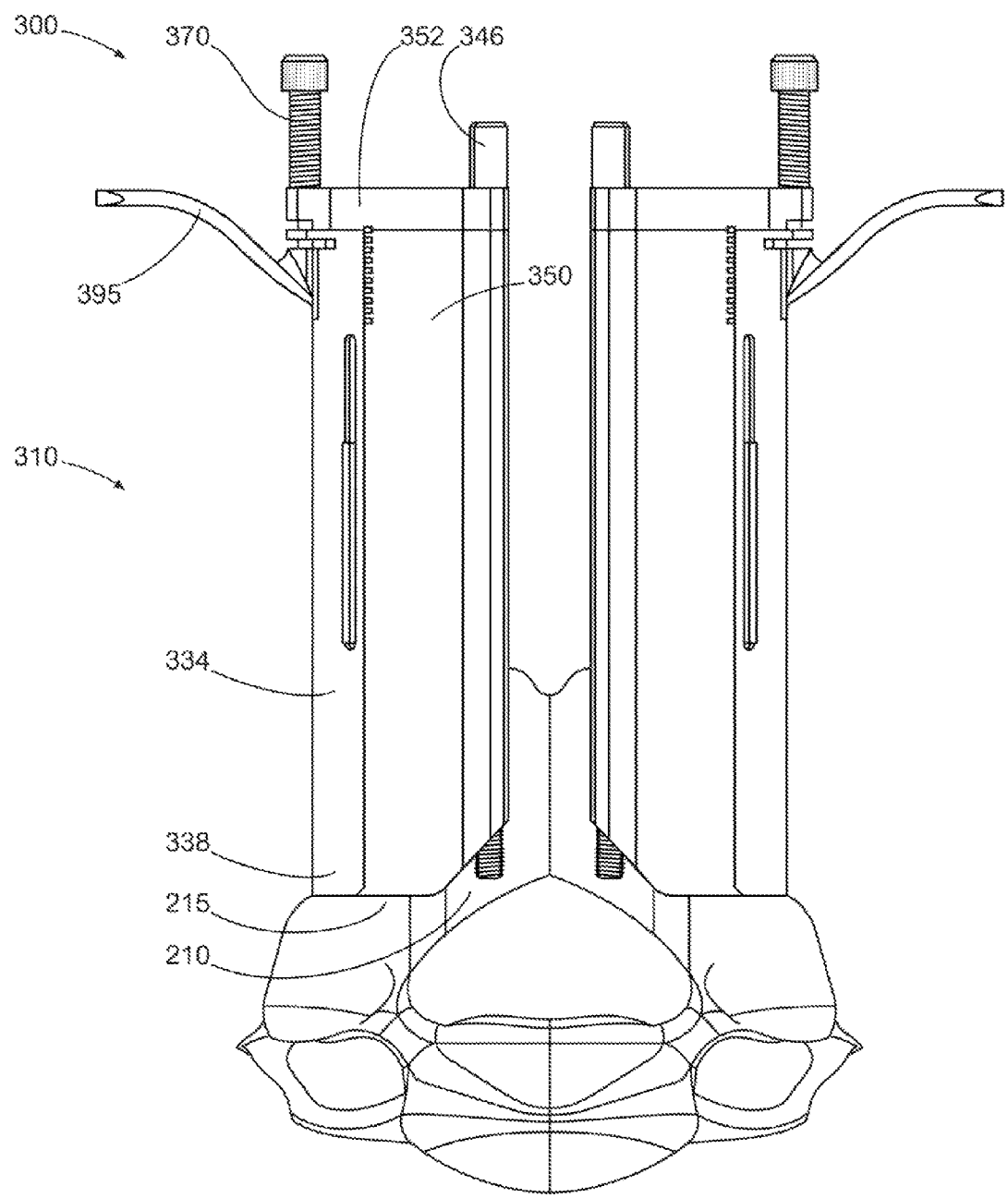
FIG. 9 is a side elevational view of two lamina setting tools in-situ and in the first position.
Figure 10:
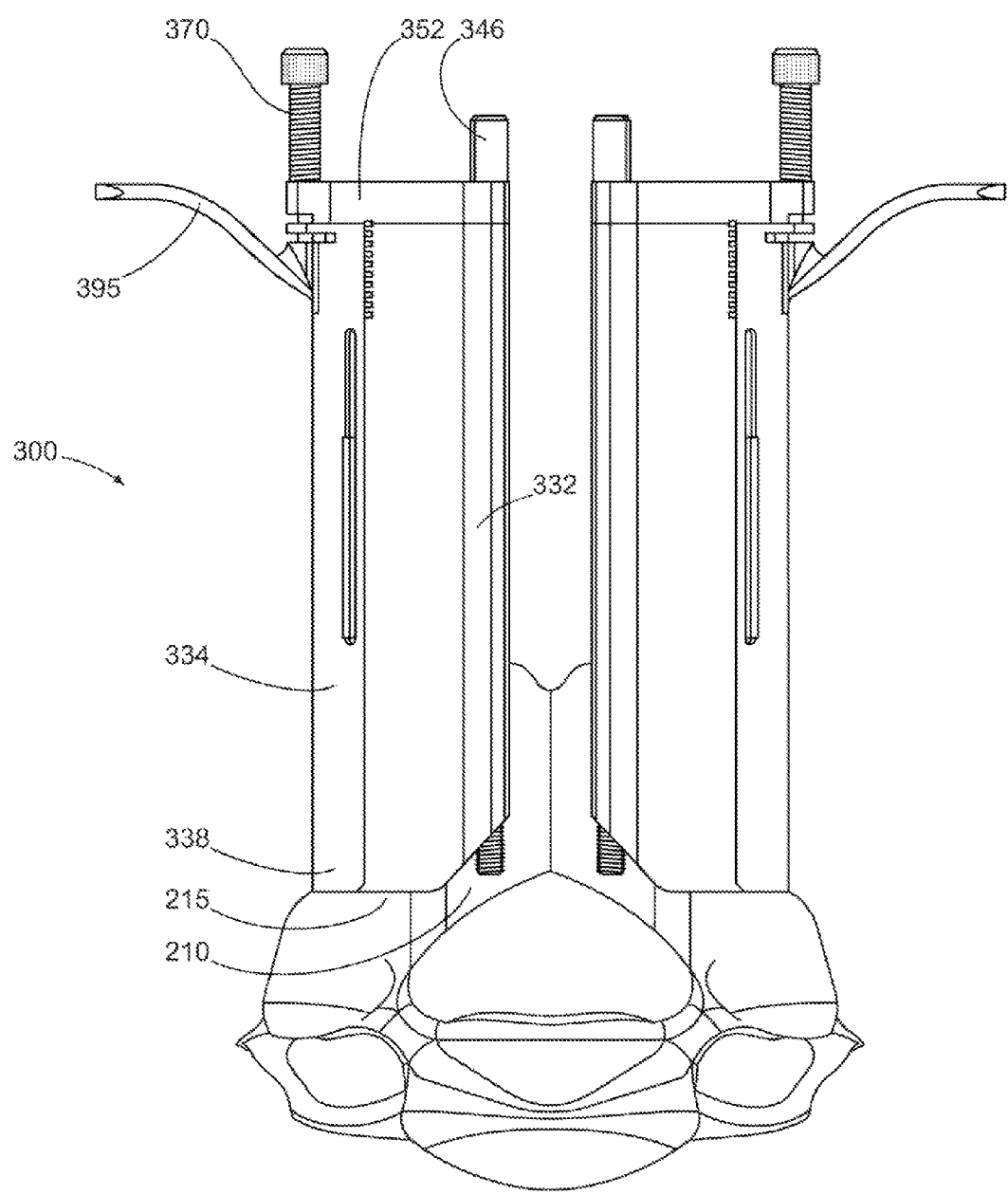
FIG. 10 is a side elevational view of two lamina setting tools in-situ and in the first position, showing a first and second sagittal division in the two lamina portions.
Figure 11:
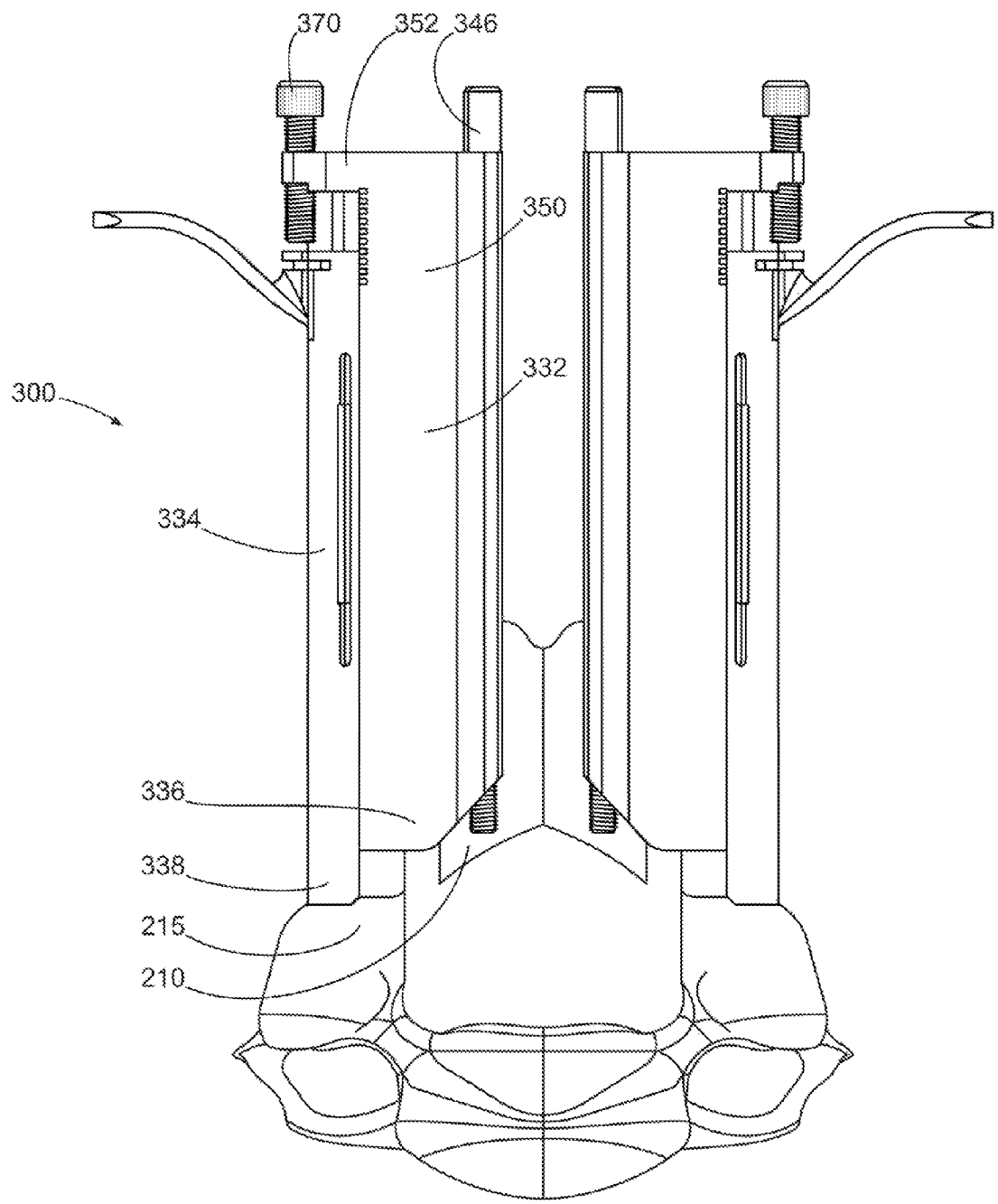
FIG. 11 a side elevational view of two lamina setting tools in-situ and in the second, elevated, position
Figure 12:
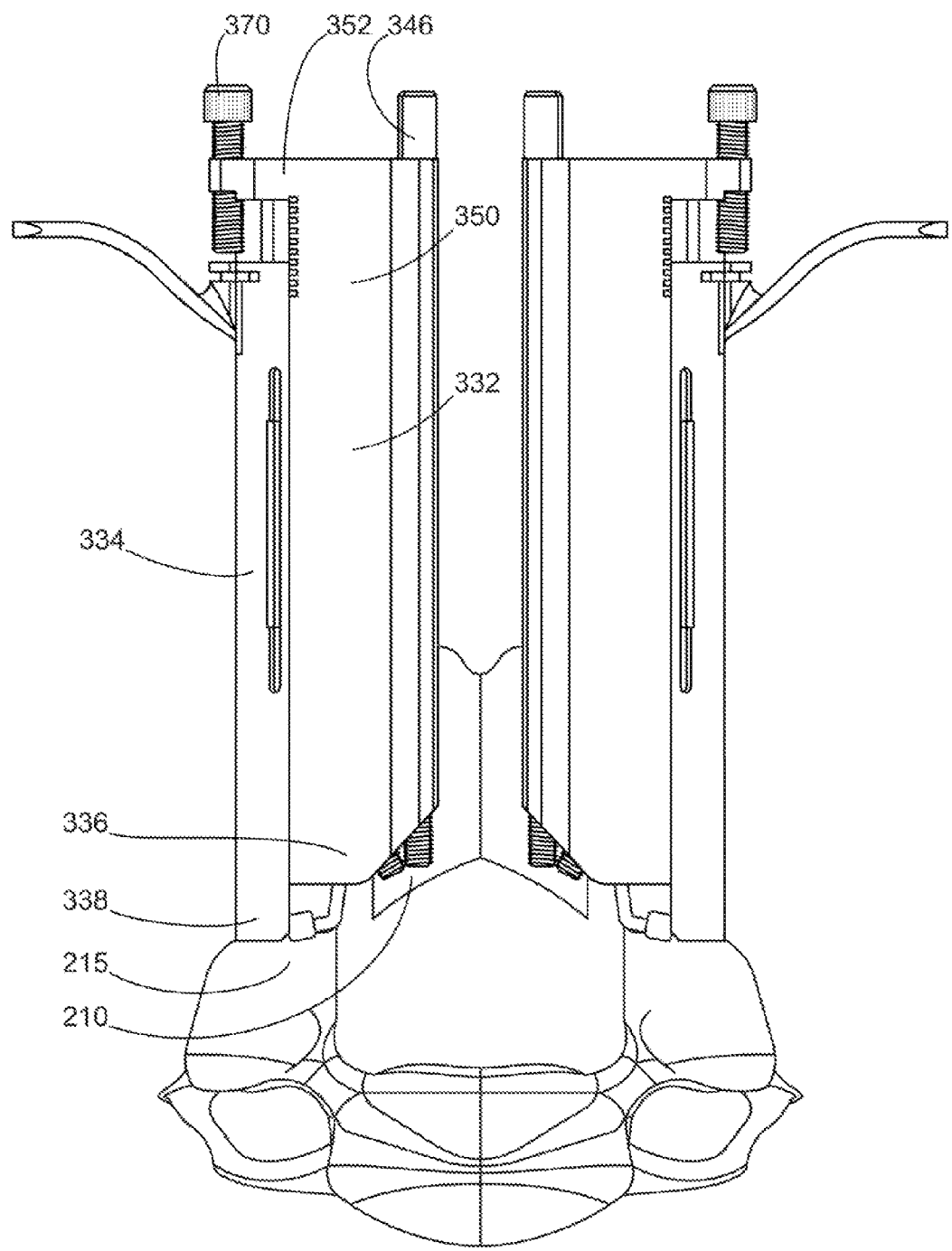
FIG. 12 is a side elevational view of two lamina setting tools in-situ and in the second position, showing placement of two laminoplasty plates.
Figure 13:
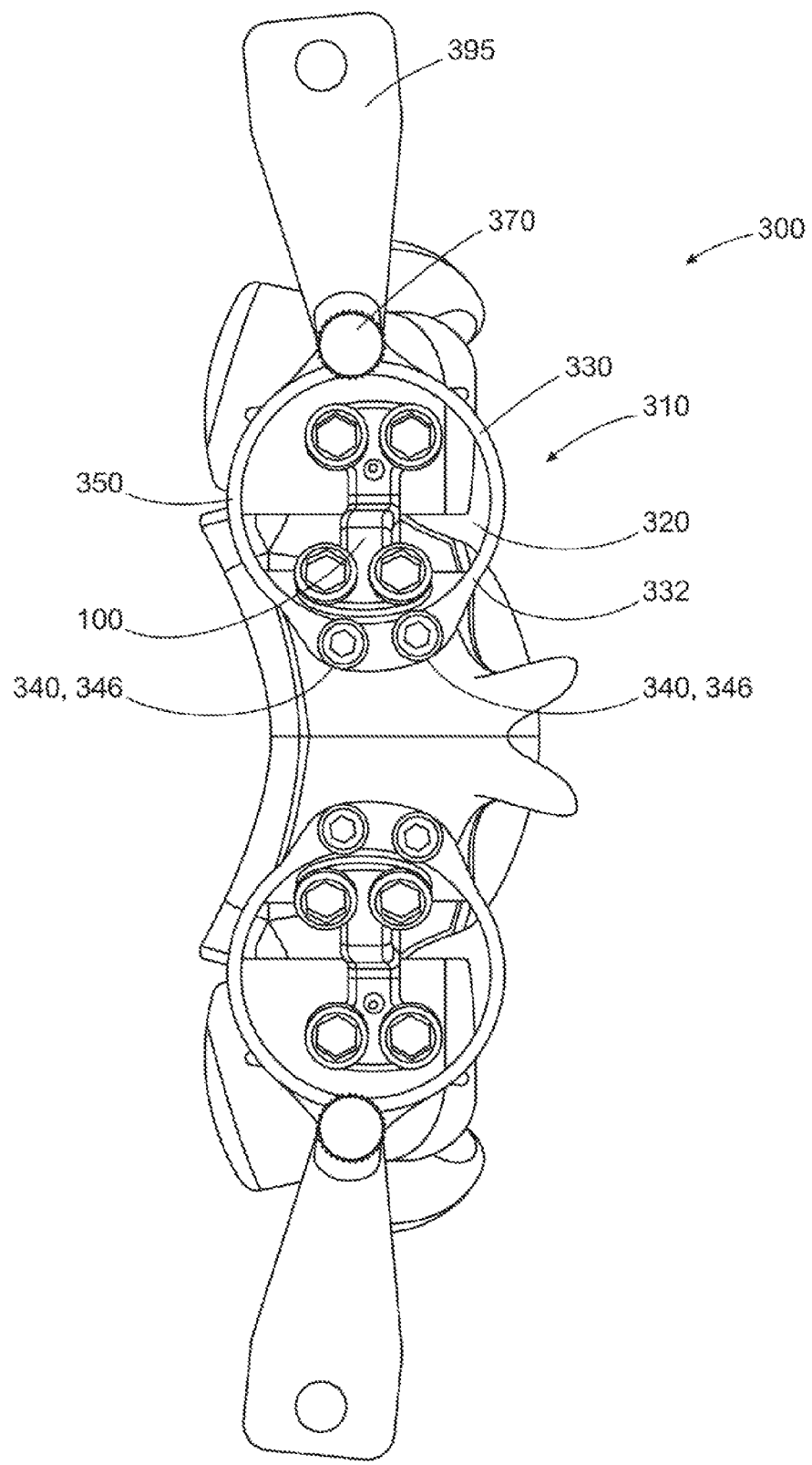
FIG. 13 is a top plan view of one aspect of a laminoplasty system showing two lamina setting tools and two laminoplasty plates.

In one aspect, presented herein is a laminoplasty plate 100 for securing a separated lamina portion 210 of a desired cervical vertebra 200 in a relief position, as shown in FIGS. 2 and 3. In one aspect, the laminoplasty plate 100 comprises a proximal end portion 110 having a bottom surface 120 defined in a first plane $P_1$ and a distal end portion 105 having a bottom surface 120 defined in a second plane $P_2$. In this aspect, the first and second planes are spaced from one another at the medial portion 130 such that the bottom surface of the proximal end portion 110 is spaced from the bottom surface of the distal end portion 105. In one exemplified aspect, the first plane is spaced a predetermined distance of between about 1 mm and about 10 mm. In another example, the first and second planes are spaced between about 3 mm and about 7 mm. In one aspect, the laminoplasty plate can be comprised of biocompatible materials such as, and not meant to be limiting, titanium, titanium alloys, surgical steel, polymeric material, ceramic material, carbon fiber composite, resorbable material, polyglyconate, autograft bone, allograft bone, xenograft bone, and hydroxy-apatite.

In one exemplified aspect, the first plane $P_1$ can be substantially parallel to the second plane $P_2$. Alternatively, the first plane can be at an acute angle α relative to the second plane. Preferably, the acute angle is between about 0 degrees and 89 degrees, and more preferably between about 0 degrees and 30 degrees. In another aspect, the laminoplasty plate can comprise a medial portion 130 that is connected to the proximal end portion and the distal end portion. In one exemplified aspect, the medial portion 130 can be arcuate in shape. In another example, the medial portion can have a reduced cross-sectional area relative to the cross-sectional areas of the distal and proximal end portions. As one skilled in the art will appreciate, this reduced cross-sectional area permits the medial portion to be more fully surrounded by bone fusion material. In a further example, the medial portion can be comprised of a substantially rigid material and have an increased cross-sectional area relative to the cross-sectional areas of the distal and proximal end portions. As one skilled in the art will appreciate, this rigidity and increase in cross-sectional area make the laminoplasty plate 100 more resistant to tensile, compressive, or shear loads while allowing the distal and proximal end portions to remain substantially flat.

In one aspect, the laminoplasty plate defines a plurality of bores 140 of pre-determined diameters. In one exemplified aspect, the proximal end portion 110 defines two paired and opposing screw bores 140 that extend substantially transverse therethrough the proximal end portion between the top and bottom surfaces of the proximal end portion and that are configured to operatively receive screws. In another aspect, the proximal end portion also defines a tool screw aperture 150 that extends substantially transverse therethrough the proximal end portion between the top and bottom surfaces of the proximal end portion and is configured to operatively receive a portion of a lamina setting tool 300. In another aspect, the tool screw aperture can be positioned therebetween the pair of screw bores of the proximal end portion. In this aspect, it is contemplated that the tool screw aperture can be positioned adjacent to and equidistant from each screw bore. In a further aspect, the distal end portion defines two paired opposing bores that extend substantially transverse therethrough the distal end portion between the top and bottom surfaces of the distal end portion and is configured to operatively receive screws. It is contemplated that different quantities and positions of the bores of the laminoplasty plate can be used in the present invention.

In one aspect, the distal end portion is comprised of a mountable portion 160 configured for detachably mounting a guide 330. In one exemplified aspect, the mountable portion 160 can be comprised of a raised cone portion to which the guide 330 can be mounted. In another example, the mountable portion can define a cavity to which the guide can be mounted. In another aspect, the mountable portion can define a tool bore 170 for receipt of a portion of the lamina setting tool. In another aspect, the mountable portion can be positioned therebetween the pair of screw bores 140 of the distal end portion 105. In this aspect, it is contemplated that the mountable portion can be positioned adjacent to and equidistant from each screw bore. Further, it is contemplated that different positions and configurations of the mountable portion of the laminoplasty plate 100 can be used in the present invention.

In yet another exemplified aspect, a lamina setting tool 300 is presented for positioning the lamina portion 210 of the desired cervical vertebra 200 in the relief position. In one aspect, the tool comprises a substantially enclosed conduit 310 defining an interior channel 320 and a circumferential sidewall 330. In one aspect, the circumferential sidewall 330 comprises a first sidewall section 332 and an opposed second sidewall section 334, where the first sidewall section 332 and second sidewall section 334 are configured to slide longitudinally with respect to one another. In this fashion, in a first position, the distal ends of the two sidewall sections 336, 338 are substantially coextensive and against the first lamina portion and the first lateral mass portion. By coextensive, it is meant that the distal ends of the first and second sidewalls, in the first position, extend about the same amount such that they lie in a plane that is substantially transverse to the longitudinal axis of the interior channel.

The interior channel 320 can be used as a portal through which a drill or other tool may be used to perform a sagittal division of the first lamina portion 210. As such, the interior channel is configured to be a portal, sized for receipt of necessary tools, such as, but not limited to, a surgical drill bit.

In an exemplified aspect, the first sidewall section comprises an anchor 340 to substantially affix the distal end 336 of the first sidewall section to the first lamina portion. In one aspect, the first sidewall section 332 can comprise at least one elongate anchor 340 that has a threaded distal end 344 configured to be driven into the first lamina portion and anchor the first sidewall section thereto. In another aspect, the first sidewall section 332 can comprise at least one elongate anchor conduit 342 configured for receipt of the elongate anchor 340. The anchor conduit 342 can be integral with the first sidewall section, external, internal, or adjacent thereto. As can be appreciated, the proximal end 346 of the elongate anchor can be keyed for receipt of a drive tool used to drive the anchor into the first lamina portion 210. In still another aspect, the first sidewall section 332 can comprise a plurality of anchor conduits and/or elongate anchors.

It is contemplated that the first sidewall section and the second sidewall section each comprise half of the tubular sidewall. It is also contemplated that the cross-section of the first sidewall section comprises a minor arc and the cross-section of the second sidewall comprises a complimentary major arc, or vice-versa, although it is not necessary that the lamina setting tool comprise a cylindrical shape. In yet another aspect, the second sidewall section may comprise a leg 395 or other means by which to affix the laminoplasty portal to a fixed structure, such as a surgical table. It is contemplated that the tube may be of different cross-sectional shape other than generally circular, such as square, elliptical, ovoid, polygonal, rectangular, etc.

As mentioned herein above, the first sidewall section 332 is configured to slide longitudinally with respect to the second sidewall section. There are several manners in which the first sidewall section can be mechanically raised with respect to the second sidewall section 334. For example, a portion of the second sidewall section can comprise teeth, while a worm gear can be mounted thereon a portion of the first sidewall section 332, or vice-versa. As such, rotation of the worm gear controllably raises the first sidewall section with respect to the second sidewall section.

In another aspect, the proximal end 350 of the lamina setting tool is circumferentially integral and integral with the first sidewall section. In this aspect, the proximal end 354 of the second sidewall section 334 can be substantially adjacent a portion of the proximal end 352 of the first sidewall section 332 in the first position. In the second position, the proximal end of the second sidewall section can be spaced therefrom the proximal end of the first sidewall section. In this aspect, the proximal end 350 of the lamina setting tool can comprise an internally threaded aperture 360 with a longitudinal axis that substantially intersects at least a portion of the second sidewall section 334. The lamina setting tool, in this aspect, also comprises an externally threaded elongate shaft 370, where the external threads are matingly complimentary to the internal threads of the aperture 360 in the proximal end 352 of the first sidewall section. In one aspect, the distal portion 372 of the externally threaded shaft 370 is mounted to a portion of the second sidewall section, but in a manner where it is permitted to freely rotate. In operation, rotation of the externally threaded shaft 370 raises the first sidewall section 332 with respect to the second sidewall section 334. As the first lamina portion 210 is raised, the distal end 336 of the first sidewall section raises along with it to a second position, leaving the distal end 338 of the second sidewall section substantially adjacent the first lateral mass portion 215 and displaced from the distal end of the first sidewall section. Since the first sidewall section 332 is affixed to the first lamina portion via the elongate anchor, raising the first sidewall section in this manner also raises the first lamina portion 210 in a controlled manner.

There are several means contemplated for permitting the two sidewall sections to longitudinally slide with respect to one another. The side edges of the two sidewalls can mate in several known fashions. In one aspect, one of the first or second sidewall sections comprises at least one longitudinal slot 380, while the other of the first or second sidewall sections comprises a complimentary longitudinal ridge 390 that fits within and slides with respect to the respective longitudinal slot 380. In another aspect, the longitudinal ridge 390 is longitudinally shorter than the respective slot such that the ridge itself acts as a stop when the first sidewall section has been slid with respect to the second sidewall section 334 a predetermined distance.

In an exemplified aspect, the distal ends of the first and second sidewall sections 336, 338 can be shaped to substantially conform to the area substantially near the first lamina portion and the first lateral mass portion. In one aspect, the distal end of the first sidewall section 332 is angled to substantially mate with the first lamina portion.

In a further aspect, the lamina setting tool can be comprised of biocompatible materials such as, and not meant to be limiting, titanium, titanium alloys, surgical steel, polymeric material, ceramic material, carbon fiber composite, resorbable material, polyglyconate, autograft bone, allograft bone, xenograft bone, and hydroxy-apatite.

Also presented herein are methods of treating cervical stenosis in a patient by relieving spinal cord compression. In one aspect, at least a portion of the desired cervical vertebra, which defines a spinal canal 240 having a pre-operative cross-sectional area, is exposed. To do so, in one aspect, a posterior incision in the patient over an area of cervical stenosis of the patient is made to expose the posterior side of the desired cervical vertebra. In this aspect, a small pathway, ranging from about 14 to 18 mm, can be dilated through the soft tissue to reach the desired cervical vertebra 200 so that muscle and tissue damage is kept to a minimum. In another aspect, the spine may be exposed more extensively in the traditional open approach.

In another aspect, the first lamina portion 210 of the desired cervical vertebra is separated. In one exemplified aspect, the step of separating the first lamina portion 210 of the desired cervical vertebra comprises making a first sagittal division 225 from the exterior of the desired cervical vertebra to the spinal canal on a first side of the midline of the vertebra and making a second sagittal division 227 from the exterior of the desired cervical vertebra to the spinal canal on a second side of midline 260. Thus, the lamina portion 210 of the desired cervical vertebra 200 and the spinous process 270 will no longer be attached at any point to the remainder of the desired cervical vertebra. In one aspect, the first and second sagittal divisions are made at the junction between the lamina portion and the lateral mass portion.

In another aspect, the first lamina portion 210 is controllably elevated to a relief position in which the spinal canal of the desired cervical vertebra has a relief cross-sectional area that is greater than the pre-operative cross-sectional area, wherein the first lamina portion is subsequently secured in an elevated position. In this aspect, after providing at least one laminoplasty plate, the step of controllably raising the first lamina portion 210 to a relief position can first comprise attaching at least a portion of the distal end portion of a first laminoplasty plate to a portion of the first lateral mass portion of the desired cervical vertebra adjacent the first sagittal division 225 and attaching at least a portion of the proximal end portion of the first laminoplasty plate to a first lamina portion adjacent the first sagittal division. In this aspect, a pre-determined length of the medial portion 130 of the laminoplasty plate 100 can correspond to the amount of separation needed between lamina portion and the desired cervical vertebra. The step of controllably raising the second lamina portion 215 to the relief position can then comprise attaching at least a portion of the distal end portion of a second laminoplasty plate to a second lateral mass portion of the desired cervical vertebra adjacent the second sagittal division 227 and attaching at least a portion of the proximal end portion 110 of the second laminoplasty plate to a second lamina portion adjacent the second sagittal division. In one exemplified aspect, the laminoplasty plates can be attached to the desired lateral mass portion and lamina portion with screws. In this example, the screws can be conventional self-tapping bone screws. It is also contemplated that conventional non-self-tapping bone screws can be used in the method of the present invention. In one aspect, the step of attaching the distal end portion 105 of the laminoplasty plates to the desired cervical vertebra comprises attaching the distal end portion of the laminoplasty plates to the respective lateral mass of the cervical vertebra. It is also contemplated that the steps of the method described herein can be completed on the first side of the midline and the second side of the midline simultaneously, sequentially, or in an alternating fashion.

The method of treating cervical stenosis in a patient by relieving spinal cord compression described herein above can be performed with this lamina setting tool. In one aspect, a posterior incision in the patient over an area of cervical stenosis of the patient is made to expose the posterior side of the desired cervical vertebra. In this aspect, the lamina setting tool is placed to position the distal end of the first sidewall section adjacent the first lamina portion and the distal end of the second sidewall section adjacent the first lateral mass portion.

At this point, in one aspect, the at least one elongate anchor 340 is driven into the first lamina portion to affix the first sidewall section to the first lamina portion. The distal end portion of the laminoplasty plate is then secured to the first lateral mass portion using screws or other fasteners placed through the bores on the distal end portion of the laminoplasty plate. In another aspect, the first lamina portion of the desired cervical vertebra is separated by making the first sagittal division using a drill or other tool therethrough the interior channel 320 of the lamina setting tool.

In an exemplified aspect, rotation of the externally threaded shaft 370 raises the first sidewall section to the second position and the first lamina portion to the relief position. Once the lamina is raised to the relief position, it can be secured into position by placing screws into the screw bores on the proximal end portion of the laminoplasty plate. Once secured, the elongate bone screw shaft can be removed, as well as the elongate guide. As one skilled in the art can appreciate, these steps can be varied with respect to sequence by the surgeon, as need. The method can also be performed bilaterally or using the aforementioned open door procedure. In this case, the procedure may be performed one after the other, simultaneously or in step-wise manner on both sides.

In one exemplified aspect, a graft (not shown) is placed proximate at least a portion of the distal and proximal end portions of the plurality of laminoplasty plates to allow fusion of the lamina portion in the relief position. In this example, the graft can be configured to surround at least a portion of the medial portion of the laminoplasty plates. In a specific example, the medial portion of the laminoplasty plate can be of reduced cross-sectional area relative to the distal and proximal end portions, and the graft can be substantially U-shaped to substantially surround the medial portion of the laminoplasty plate. Further, the graft can be composed of autologous bone, allograft bone, synthetic bone substitute, and osteoinductive agent.

It is also anticipated that a tube system such as this may be useful in other procedures in which the benefit of having two or more sliding portions of a tube system will aid in the efficient exclusion of tissue from the interior of the tube. Additionally, it is anticipated that a tube may optionally be secured to the area of interest in the procedure by a stabilizing arm or other element on the tube system that can be connected to the operating table through an intermediate connection and/or attached to the desired vertebra or bone via one or more attachment members, such as a threaded post into a stable portion of the bone.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A laminoplasty system comprising:
    a laminoplasty plate for securing a separated lamina portion of a desired cervical vertebra in a relief position; and
    a lamina setting tool comprising:
        a substantially enclosed conduit defining an interior channel and a substantially circumferential sidewall having a first sidewall section having a proximal end and a distal end, and an opposed second sidewall section, having a proximal end and a distal end, wherein the first sidewall section is configured to slide longitudinally with respect to the second sidewall section, and wherein, the first sidewall section is selectively movable from a first position where the distal ends of the first and second sidewall sections are substantially coextensive, to a second position, where the distal end of the first sidewall section is raised with respect to the distal end of the second sidewall section, whereby, when the first sidewall section is raised, it raises the separated lamina portion therewith.

2. The laminoplasty system of claim 1, wherein the distal end of the first side wall section is configured to attach to a lamina portion, and wherein the distal end of the second sidewall section is configured to abut a lateral mass portion.

3. The laminoplasty system of claim 2, further comprising means to perform a sagittal division, separating the lamina portion from the lateral mass portion.

4. The laminoplasty system of claim 3, wherein the conduit is configured to be used as a portal through which a tool may be used to perform the sagittal division.

5. The laminoplasty system of claim 3, wherein, when the lateral mass portion is separated from the lamina portion, raising the distal end of the first sidewall section raises the lamina portion to the relief position.

6. The laminoplasty system of claim 2, wherein the first sidewall section comprises an anchor to substantially affix the distal end of the first sidewall section to the lamina portion.

7. The laminoplasty system of claim 1, wherein a proximal end of the lamina setting tool is circumferentially integral and integral with a proximal end of the first sidewall section.

8. The laminoplasty system of claim 7, wherein a proximal end of the second sidewall section is substantially adjacent a portion of the proximal end of the first sidewall section in the first position.

9. The laminoplasty system of claim 8, wherein the proximal end of the lamina setting tool comprises an internally threaded aperture with a longitudinal axis that substantially intersects at least a portion of the second sidewall section.

10. The laminoplasty system of claim 9, further comprising an externally threaded elongate shaft having external threads which are matingly complimentary to the internal threads of the aperture in the proximal end of the first sidewall section, and wherein a distal portion of the externally threaded elongate shaft is mounted to a portion of the second sidewall section whereby it is permitted to freely rotate, and wherein, in operation, rotation of the externally threaded elongate shaft raises the first sidewall section with respect to the second sidewall section to the relief position in a controlled manner.

11. The laminoplasty system of claim 1, wherein one of the first or second sidewall sections comprises at least one longitudinal slot and the other of the first or second sidewall sections comprises a complimentary longitudinal ridge that fits within and slides with respect to the respective longitudinal slot, and wherein the longitudinal ridge is longitudinally shorter than the respective slot such that the ridge acts as a stop when the first sidewall section has been slid with respect to the second sidewall section a predetermined distance.

12. The laminoplasty system of claim 2, wherein the distal ends of the first and second sidewall sections are shaped to substantially conform to an area substantially near the lamina portion and the lateral mass portion.

13. The laminoplasty system of claim 12, wherein the distal end of the first sidewall section is angled to substantially mate with the lamina portion.

14. A lamina setting tool for use with a laminoplasty plate for securing a separated lamina portion of a desired cervical vertebra in a relief position, the lamina setting tool comprising:
    a substantially enclosed conduit defining an interior channel and a substantially circumferential sidewall having a first sidewall section having a proximal end and a distal end, and an opposed second sidewall section, having a proximal end and a distal end, wherein the first sidewall section is configured to slide longitudinally with respect to the second sidewall section, and wherein, the first sidewall section is selectively movable from a first position where the distal ends of the first and second sidewall sections are substantially coextensive, to a second position, where the distal end of the first sidewall section is raised with respect to the distal end of the second sidewall section whereby, when the first sidewall section is raised, it raises the separated lamina portion therewith.

15. The lamina setting tool of claim 14, wherein the distal end of the first side wall section is configured to attach to a lamina portion, and wherein the distal end of the second sidewall section is configured to abut a lateral mass portion.

16. The lamina setting tool of claim 15, further comprising means to perform a sagittal division, separating the lamina portion from the lateral mass portion, wherein the conduit is configured to be used as a portal through which a tool may be used to perform the sagittal division.

17. The lamina setting tool of claim 16, wherein, when the lateral mass portion is separated from the lamina portion, raising the distal end of the first sidewall section raises the lamina portion to the relief position.

18. The lamina setting tool of claim 16, wherein the first sidewall section comprises an anchor to substantially affix the distal end of the first sidewall section to the lamina portion.

19. The lamina setting tool of claim 15, wherein a proximal end of the lamina setting tool is circumferentially integral and integral with a proximal end of the first sidewall section, and wherein a proximal end of the second sidewall section is substantially adjacent a portion of the proximal end of the first sidewall section in the first position.

20. The lamina setting tool of claim 19, wherein the proximal end of the lamina setting tool comprises an internally threaded aperture with a longitudinal axis that substantially intersects at least a portion of the second sidewall section.

21. The lamina setting tool of claim 20, further comprising an externally threaded elongate shaft having external threads which are matingly complimentary to the internal threads of the aperture in the proximal end of the first sidewall section, and wherein a distal portion of the externally threaded elongate shaft is mounted to a portion of the second sidewall section whereby it is permitted to freely rotate, and wherein, in operation, rotation of the externally threaded elongate shaft raises the first sidewall section with respect to the second sidewall section to the relief position in a controlled manner.

22. The lamina setting tool of claim 15, wherein one of the first or second sidewall sections comprises at least one longitudinal slot and the other of the first or second sidewall sections comprises a complimentary longitudinal ridge that fits within and slides with respect to the respective longitudinal slot, and wherein the longitudinal ridge is longitudinally shorter than the respective slot such that the ridge acts as a stop when the first sidewall section has been slid with respect to the second sidewall section a predetermined distance.

23. The lamina setting tool of claim 15, wherein the distal ends of the first and second sidewall sections are shaped to substantially conform to an area substantially near the lamina portion and the lateral mass portion.

24. The lamina setting tool of claim 23, wherein the distal end of the first sidewall section is angled to substantially mate with the lamina portion.

25. A method of treating cervical stenosis in a patient by relieving spinal cord compression, the method comprising:
providing a lamina setting tool comprising a substantially enclosed conduit defining an interior channel and a substantially circumferential sidewall having a first sidewall section having a proximal end and a distal end, and an opposed second sidewall section, having a proximal end and a distal end, wherein the first sidewall section is configured to slide longitudinally with respect to the second sidewall section, and wherein, the first sidewall section is selectively movable from a first position where the distal ends of the first and second sidewall sections are substantially coextensive, to a second position, where the distal end of the first sidewall section is raised with respect to the distal end of the second sidewall section;
exposing at least a portion of a posterior side of a desired cervical vertebra of the patient, the cervical vertebra having a midline;
affixing the distal end of the first side wall section to a lamina portion;
separating a lamina portion of the posterior side of the desired cervical vertebra on a first side of the midline substantially at a junction between the lamina portion and a lateral mass portion using the conduit of the lamina setting tool as a portal;
providing at least one laminoplasty plate;
securing a first portion of the at least one laminoplasty plate to the lateral mass portion adjacent the partial first sagittal division;
raising the lamina portion to a relief position by raising the first sidewall section with respect to the second sidewall section;
securing a second portion of the at least one laminoplasty plate to a portion of the lamina portion in the relief position; and
removing the lamina setting tool.

* * * * *